United States Patent [19]

Bjursten et al.

[11] Patent Number: 5,152,993

[45] Date of Patent: Oct. 6, 1992

[54] METHOD OF PREPARING AN IMPLANT BODY FOR IMPLANTATION

[75] Inventors: Lars-Magnus Bjursten, Malmo; Pentti Tengvall; Ingemar Lundstrom, both of Linkoping, Sweden

[73] Assignee: Ellem Bioteknik AB, Sweden

[21] Appl. No.: 555,987

[22] Filed: Jul. 18, 1990

Related U.S. Application Data

[63] Continuation-in-part of Ser. No. 411,466, Sep. 19, 1989, Pat. No. 5,045,318.

[30] Foreign Application Priority Data

Jan. 20, 1988 [SE] Sweden .............................. 8800176
Jul. 19, 1989 [SE] Sweden .............................. 8902565

[51] Int. Cl.⁵ .................... A61F 2/00; A01N 59/16
[52] U.S. Cl. .............................. 424/422; 424/423; 424/613; 424/617; 423/598; 623/16; 623/66
[58] Field of Search ............... 424/422, 423, 613, 617; 423/584, 598; 623/16, 66

[56] References Cited

U.S. PATENT DOCUMENTS

| | | | |
|---|---|---|---|
| 4,305,926 | 12/1981 | Everse et al. | 424/14 |
| 4,615,705 | 10/1986 | Scales | 623/11 |
| 4,828,563 | 5/1989 | Lierheim | 623/16 |
| 4,975,526 | 12/1990 | Kuberasampath | 530/350 |

FOREIGN PATENT DOCUMENTS 222498  5/1985  German Democratic Rep. .
2106765  5/1987  Japan .

Primary Examiner—Thurman K. Page
Assistant Examiner—G. S. Kishore
Attorney, Agent, or Firm—Ostrolenk, Faber, Gerb & Soffen

[57] ABSTRACT

A method of preparing an implant body in order to optimize the healing time of said implant, comprising bringing the implant body for a limited period of time into contact with a hydrogen peroxide solution at least on the surfaces intended to come into contact with surrounding tissue when implanted, the treated surfaces being cleaned by rinsing. The treatment of the implant surface with hydrogen peroxide can be supplemented with incorporation of biomolecules, such as peptides, proteins and steroids, and also other substances such as inorganic ions and crystals. The compounds to be coupled to the implant surface may promote the healing and/or binding of the surrounding tissue.

9 Claims, No Drawings

METHOD OF PREPARING AN IMPLANT BODY FOR IMPLANTATION

This application is a continuation-in-part of application Ser. No. 411,466, filed Sept. 19, 1989 now U.S. Pat. No. 5,045,318 the disclosure of which is hereby incorporated by reference.

BACKGROUND OF THE INVENTION

This application is a continuation-in-part of application Serial No. 411,466 filed Sept. 19, 1989, now U.S. Pat. No. 5,045,318 the disclosure of which is hereby incorporated by reference.

The present invention relates to a method of preparing an implant body for implantation in order to optimize the healing time of said implant.

It is well known that implant bodies of titanium or implant bodies coated with titanium are particularly suitable for implantation in living tissue. Technology of this type has long been used by Professor Branemark in Gothenburg for implanting titanium screws into jaw bones, the implanted titanium screws then serving as anchorage points for artificial teeth. To obtain good results, the actual oxide layer on the surface of the implant should exhibit special properties with respect to surface energy, dielectric constant, corrosion resistance, $pK_a$ and degree of hydration. It has also been found that the phenomena appearing during the period immediately after implantation are of the utmost importance in establishing biointegration. During this period, it must be possible to induce the inevitable inflammatory reaction caused by the surgical incision to heal suitably. This initial inflammatory reaction to the implant is characterized by the presence of cells which neutralize and degrade foreign objects since these cells produce tissue-degrading enzymes, free oxygen radicals and $H_2O_2$ and have the ability to engulf foreign particles. Clinical experiments have shown that some of the oxygen radicals produced are extremely dangerous to living tissue.

The object of the invention is to provide a method for preparing an implant body for implantation such that that the healing time following the implantation is optimized, thereby avoiding the above-mentioned risks.

SUMMARY OF THE INVENTION

This object is achieved according to the invention by contacting the implant body for a limited period of time with a hydrogen peroxide solution at least on the surfaces intended to come into contact with surrounding tissue when implanted, the treated surfaces then being cleaned by rinsing.

This may be done, for instance, by immersing the implant surfaces in a hydrogen peroxide solution, by painting or spraying them with such a solution, in which case this treatment can be performed immediately prior to implantation, or a relatively long time before implantation, in which case, however, the implant body must be stored in a inert environment until is to be used for implantation. The hydrogen peroxide treatment results in the formation of a surface layer containing hydrated oxide, peroxide and superoxide.

A 1-30% solution of hydrogen peroxide is suitably used as treating liquid.

Biomolecules may be incorporated into the surface layer during or after the hydrogen peroxide treatment. Inorganic ions and/or crystals may also be incorporated into that layer.

DETAILED DESCRIPTION OF THE INVENTION

When performing the invention, a body of titanium or a body coated with a layer or titanium, for instance, may be immersed in a 10% solution of hydrogen peroxide for 20 minutes, after which the body is carefully rinsed with water. The body treated in this manner may be used immediately or, alternatively, stored in a non-reducing environment until it is to be used for implantation.

The immersion in hydrogen peroxide cleans the titanium surfaces and at the same time a reaction probably occurs between $H_2O_2$ and $O_2$ with titanium (III) or titanium (IV) ions leaching out at the oxidized titanium surface. A catalytic decomposition of the excess peroxide then occurs and a surface layer of hydrated oxide with peroxide and superoxide incorporated in a polymeric structure is obtained, the surface layer being in the form of a gel-like coating.

This gel-like coating, the preparation and nature of which is discussed in application Ser. No. 411,466, now U.S. Pat. No. 5,045,318 above referred to and incorporated by reference, decomposes by chemical reduction to hydrogen peroxide and titanium hydroxide and the gel thus acts as a slow-release hydrogen peroxide reservoir.

The implant surfaces so coated have an inhibiting effect on inflammatory activity and also exhibit an ability to oxidize thiol groups.

The treatment according to the invention thus achieves cleansing, disinfection and saturation of the oxide layer with respect to hydrated titanium oxide.

The treatment time with the hydrogen peroxide solution is, of course, dependent on interaction between the concentration of the solution and the effective treatment time. A minimum treatment of 1 minute and preferably not more than 30 minutes is generally sufficient.

The rinsing agent used according to the invention is preferably water or a salt solution.

An implant body conditioned according to the invention can be stored for up to six months in an inert environment such as water.

Favorable healing is obtained even in the case of implant of material other than titanium, primarily thanks to the cleansing action of the hydrogen peroxide on the implant body. The surface will also be conditioned due to the action of the oxygen radicals released from the hydrogen peroxide. This treatment can be compared to the glow discharge plasma treatment used to optimize the surface in tissue-cultivation dishes of polystyrene, for instance.

The suggested treatment of the implant surface with hydrogen peroxide can be supplemented with the incorporation of biomolecules promoting the healing response of the surrounding tissue. Such molecules include peptides, proteins and steroids. The biomolecules may either be added during or after the hydrogen peroxide treatment but before a rinsing procedure by e.g., water, saline or serum is performed. The conditions for the incorporation procedure are determined by titration of the biomolecule to determine its stability to e.g., hydrogen peroxide and the pH of the treating environment. After exposure to $H_2O_2$, the Ti-surface has incorporated oxidizing $Ti(IV)O_2$ groups to the outermost oxide layer. These reactive groups are able to oxidize biomolecules containing thiol (—SH) or protein aminoterminals (—NH$_2$) thereby covalently binding them to the Ti-surface via hydroxyl (—OH) group displacement and concomitant water cleavage for the oxide. The procedure is applicable in the pH range 2-7, depending on the charge of the biomolecule.

Another way to modify the implant surface to induce a more favorable healing response in any tissue but especially in bone tissue is to incorporate inorganic ions and/or crystals into the surface layer by adding these to the solution containing hydrogen peroxide. Examples of such ions are $Ca^{2+}$, $Mg^{2+}$, $Zn^{2+}$, $PO_4$ and hydroxylapatite.

The compounds to be coupled to the implant surface are intended to change the interaction of the implant with the surrounding biological environment. Thus the coupled compound promotes the healing and/or binding of the surrounding tissue. In other instances, the adhesion to the implant surface is diminished. This is of special interest for implants in contact with blood or other body fluids. Another application of this technique is for inhibiting the growth of microorganisms, such as bacteria, by the coupled compound.

Examples of compounds to be coupled to the surface to obtain the above-described properties follows:

A variety of growth factors and biological attachment molecules.

Examples of growth factors are:

NGF nerve growth factor

FGF fibroblast growth factors

CSF colony stimulating factors

Examples of attachment molecules are found among the so called integrius and nectius but may also be specific antibodies and complement factors. Molecules known to diminish adhesion are for instance heparin and some proteoglycans.

The method is however not limited to the coupling of the molecules mentioned above but includes the coupling of any compound of biological or nonbiological origin to the surface of an implant using the described procedure.

Examples of such molecules of nonbiological origin are found among the polymers, especially those with amide or thiol groups, but also others, such as polyethylene glycol, which have been shown to modify the response of the surrounding tissue.

Although the present invention has been described in relation to particular embodiments thereof, many other variations and modifications and other uses will become apparent to those skilled in the art. The present invention is to be limited not by the specific disclosure herein, but only by the appended claims.

What is claimed is:

1. A method of preparing an implant body for implantation, said implant consisting of titanium or being coated with titanium, comprising contacting the implant body with a hydrogen peroxide solution at least at the surfaces intended to come into contact with surrounding tissue when implanted, for a time sufficient to form a surface layer of hydrated oxide with peroxide and superoxide incorporated in a polymeric structure, and then rinsing said surfaces without removing said surface layer.

2. A method as claimed in claim 1, wherein said hydrogen peroxide solution is a 1-30% solution.

3. A method as claimed in claim 2, wherein said implant surfaces are immersed in said 1-30% hydrogen peroxide solution.

4. A method as claimed in claim 2, wherein said implant surfaces are painted or sprayed with said 1-30% hydrogen peroxide solution.

5. A method as claimed in claim 2, wherein, after rinsing, the implant body is stored in an inert environment until it is to be used for implantation.

6. A method as claimed in claim 5, wherein said inert environment is water.

7. A method as claimed in claim 2, wherein water or a salt solution is used as the rinsing liquid.

8. A method as claimed in claim 2, wherein the duration of contact for the implant body with the treating liquid is at least 1. minute.

9. A method as claimed in claim 8, wherein said duration of contact is 1-30 minutes.

* * * * *